United States Patent
Diesso (10) Patent No.: US 7,101,178 B2
(45) Date of Patent: Sep. 5, 2006

(54) DENTAL IMPRESSION METHOD AND DEVICE

(76) Inventor: Michael Diesso, P.O. Box 939, East Wareham, MA (US) 02538

( * ) Notice: Subject to any disclaimer, the term of this patent is extended or adjusted under 35 U.S.C. 154(b) by 0 days.

(21) Appl. No.: 10/497,981

(22) PCT Filed: Dec. 5, 2002

(86) PCT No.: PCT/US02/38752

§ 371 (c)(1),
(2), (4) Date: Jun. 4, 2004

(87) PCT Pub. No.: WO03/049635

PCT Pub. Date: Jun. 19, 2003

(65) Prior Publication Data

US 2004/0241606 A1    Dec. 2, 2004

Related U.S. Application Data

(60) Provisional application No. 60/336,991, filed on Dec. 7, 2001.

(51) Int. Cl.
A61C 9/00 (2006.01)
(52) U.S. Cl. .......................... 433/37; 433/41
(58) Field of Classification Search ................ 433/34, 433/37, 38, 41, 42, 45
See application file for complete search history.

(56) References Cited

U.S. PATENT DOCUMENTS

| | | | |
|---|---|---|---|
| 1,369,171 A * | 2/1921 | Graham | 433/42 |
| 1,584,092 A | 5/1926 | Harris | |
| 1,979,493 A | 11/1934 | Salvio | |
| 2,313,535 A | 3/1943 | Glitzke | |
| 2,583,170 A * | 1/1952 | Getz | 433/35 |
| 2,597,929 A | 5/1952 | Gorsk et al. | |
| 2,703,452 A | 3/1955 | Getz | |
| 2,713,202 A | 7/1955 | Jones | |
| 2,895,219 A | 7/1959 | Jones | |
| 3,085,337 A * | 4/1963 | Shulman | 433/38 |
| 3,468,029 A * | 9/1969 | Moore | 433/38 |
| 3,473,225 A | 10/1969 | Deuschle et al. | |
| 3,501,837 A * | 3/1970 | Clark | 433/38 |
| 3,604,116 A | 9/1971 | Shpuntoff | |

(Continued)

OTHER PUBLICATIONS

International Search Report for International Application No. PCT/US02/38752, mailed Jul. 17, 2003.

(Continued)

*Primary Examiner*—Ralph A. Lewis
(74) *Attorney, Agent, or Firm*—Barnes & Thornburg, LLP; James B. Conte (57) ABSTRACT

A dental impression device (100) which has a buccal support (1*a*), a lingual support (1*b*), and a joining section (1*c*). The buccal support (1*a*) is disposed towards the buccal side of a dental arch; the lingual support (1*b*) is disposed towards the lingual side of the dental arch; and the joining section (1*c*), which connects the buccal and lingual supports, is disposed posterior in the mouth's no bite region. The supports (1*a*, 1*b*) form impression material holding areas which hold and secure dental impression material (9). The supports (1*a*,1*b*) and joining section (1*c*) form an open bite through area through which the lower and upper teeth's occlusal surfaces can make contact. Dental impression material (9) supported in the holding area by the supports is disposed in the open bite through area and is between the occlusal surfaces of the upper and lower teeth. The dental impression is then formed by a person making a closed bite into the impression material.

11 Claims, 5 Drawing Sheets

U.S. PATENT DOCUMENTS

| | | |
|---|---|---|
| 3,903,602 A | 9/1975 | Jones |
| 4,003,132 A | 1/1977 | Beck |
| 4,204,323 A * | 5/1980 | Neubert et al. ............... 433/38 |
| 4,368,040 A | 1/1983 | Weissman |
| 4,449,927 A | 5/1984 | Taylor et al. |
| 4,619,610 A * | 10/1986 | Pelerin ....................... 433/41 |
| 4,689,010 A * | 8/1987 | Wolfe .......................... 433/38 |
| 5,102,335 A | 4/1992 | Getz |
| 5,316,474 A | 5/1994 | Robertson ................... 433/38 |
| 5,336,086 A | 8/1994 | Simmen et al. ............... 433/37 |
| 5,580,244 A | 12/1996 | White |
| 5,636,985 A | 6/1997 | Simmen et al. ............... 433/37 |
| 5,733,118 A * | 3/1998 | Pankuch et al. .............. 433/38 |
| 5,820,372 A | 10/1998 | Jones .......................... 433/38 |
| 6,079,977 A | 6/2000 | Persichetti ................... 433/37 |
| 6,206,693 B1 | 3/2001 | Hultgren |

OTHER PUBLICATIONS

Six screen shots from the web page for D & D Dental Trays showing sale of trays which applicant assumes are prior art, dnddental.freeservers.com.

\* cited by examiner

DENTAL IMPRESSION METHOD AND DEVICE

CROSS REFERENCE TO RELATED APPLICATIONS

This application is a national stage application under 35 U.S.C. 371 of International Application PCT/US02/38752 filed on Dec. 5, 2002 which claims benefit of U.S. Provisional Application 60/336,991 filed on Dec. 7, 2001.

FIELD OF THE INVENTION

The present Invention relates in general to a method and a device to impression the teeth and gums of dental arches and particularly relates to making accurate impressions of a patient's upper and lower teeth and recording the bite registration.

BACKGROUND OF THE INVENTION

Dentists use dental impression trays and cups to make impressions of teeth. Dental impressions should essentially be an exact replica, in reverse, of the existing dentition, the surrounding tissues and support structures. The impression is used to produce a gypsum model upon which a prosthetic or corrective device can be fabricated. If there are distortions or inaccuracies in the dental impression, the resultant model will be inaccurate and therefore the fabricated appliance will not fit correctly creating pain, trauma and difficulty for the patient.

Generally, dental trays, both open mouth and closed mouth, past and present, appear to have two (2) features that prevail:

1. The trays have dental impression material containment sidewalls.
2. The trays provide a tray floor or a mid-section separator sheet to section the tray into an upper and lower chamber to contain the dental impression material.

U.S. Pat. No. 310,407 discloses dental impression trays that are generally shaped to conform to a dental arch and include a trough type tray surrounded by solid impression material containment walls. The tray serves as a carrier for the impression material, it additionally serves to hold the positioned material in place through the setting process. This tray is used for open mouth dental impressions. U.S. Pat. No. 1,360,146 discloses a dental tray which may be used to capture an upper and lower partial impression and to capture the bite in one operation. This tray is U shaped and consists of opposing buccal and lingual solid sidewalls. The use of this tray is described as being suitable for closed bite partial impressions and the practical operation for use is described as mounting an impression material between the sidewalls on opposite sides of a narrow piece of a rubber dam. Effectively, this description teaches that the rubber dam, would function as a mid-section to separate the tray into an upper and lower chamber. The illustration does not show the rubber dam.

It appears that the dental tray art seeks to reduce distortion of the impression and inaccuracies in the bite registration. Distortion can occur due to biting forces. The biting forces cause the impression material to extrude in all directions placing pressure on the sidewalls of the tray causing the sidewalls to flex and remain flexed through the setting process. The walls then relax back and bring with them, to a degree the set material. Distortion of the impression can also occur due to the tray separating from the material in the process of trying to remove it from the mouth. Distortion of the impression can further occur due to the manipulation of the tray during the model preparation phase.

In addition to distortion, inaccuracies of the bite registration can occur. Inaccuracies occur due to the thickness of a separator sheet that divides the upper and lower chamber preventing the teeth from making full surface-to-surface contact.

There have been several attempts to address distortions and inaccuracies. Traditionally, it appears the attempts have followed in the direction of:

a. stronger, reinforced sidewalls, to prevent flexing;

b. perforated sidewalls to retain impression material in the tray and keep it from separating during removal from the mouth; and c. thinner separating sheets made of various preferred materials.

Examples of closed bite dental trays seeking to reduce distortion and inaccuracies are shown below in the following described patents.

U.S. Pat. Nos. 1,584,092 and 1,979,493 disclose and describe closed mouth impression trays having solid sidewalls to contain the impression material and a separator sheet that sections the tray into upper and lower chambers.

U.S. Pat. Nos. 2,313,535 and 2,597,929 disclose and describe a wire form that conforms only to the dental arch buccally. The position of metal retention clips mid-way in the central bite area would prevent the patient with posterior teeth from closing into full surface to surface, centric occlusion and render these devices as unsuitable for use as a closed bite dental impression tray.

U.S. Pat. No. 2,703,452 discloses a tray with perforated sidewalls and a separator sheet.

U.S. Pat. No. 3,468,029 discloses a closed bite impression tray that consists of two matching trays with half height sidewalls that are connected by a posterior hinge that allows the tray to be opened for insertion of a separator sheet that effectively sections the ready tray into an upper and lower chamber and secondarily allows for the tension of the separator sheet to be adjusted.

U.S. Pat. No. 3,604,116 discusses the inaccuracies of bite registrations obtained in closed bite impression trays with a separator sheet having a thickness greater than. 0.020 mm. U.S. Pat. No. 4,003,132 discloses a closed bite dental impression tray that consists of perforated sidewalls and a separator sheet that sections the tray into upper and lower material containment chambers.

U.S. Pat. No. 4,204,323 discloses a closed bite dental impression tray with perforated side walls that additionally contain an interior locking recess and a slot for placement of a separator sheet to section the tray into upper and lower material containment chambers.

U.S. Pat. No. 4,368,040 discloses a dental impression tray with a material chamber tray floor. Impression material may be injected into the tray through slotted sidewalls to obtain a dental impression insitu.

U.S. Pat. Nos. 4,449,927 and 5,820,372 disclose a two part system consisting of a bite tray holder with a pair of laterally spaced, solid side wall tray holders shaped to receive an insert-able bite tray and the insert-able bite tray with solid side walls and a separator sheet that sections the tray into upper and lower material containment chambers.

U.S. Pat. Nos. 4,619,610, 4,689,010, and 5,316,474, disclose trays with solid sidewalls with interior grip mechanisms and a separator sheet.

U.S. Pat. No. 5,636,985 discusses in length the distortion problems and discloses a tray with extra-ridged solid sidewalls and a separator sheet.

Impression trays used for open mouth impressions have followed a similar course as evidenced by U.S. Pat. Nos. 3,473,225, 5,336,086, and 6,079,977. In addition to trays used for closed bite impressions of the upper arch, lower arch and the bite registration, there are secondary dental impression trays that are used primarily to capture only the bite registration. The same problems of bite inaccuracies due to a separator sheet are prevalent. For example, U.S. Pat. Nos. 2,713,202, 2,895,219 and 3,903,602 disclose a pair of frames connected by a handle and have contained thereon, bibs for the placement of impression material. This patent does not discuss the use of the frames without the bibs. The frames do not extend vertically.

U.S. Pat. No. 4,472,140, discloses a plastic frame that partially surrounds a dental arch and contains a thin separator sheet for the placement of impression material. The frame does not extend vertically.

Finally, commercially available is an open walled dental tray fabricated of multiple 4–6 gage welded stainless steel rods. It is designed and intended to be re-useable from one patient to another by means of cleaning and sterilization.

Problems concerning distortion, retention and inaccuracies continue to exist.

SUMMARY OF INVENTION

As a solution to the above described problems, the present invention provides a device that has buccal and lingual supports. The supports surround or partially surround a dental arch buccally and lingually for the purpose of a dental impression. The supports are vertically repeating or vertically extended. The vertically extended or vertically repeating portions of the supports form impression material holding areas. The areas hold dental impression material. The portions of the supports forming the impression material holding areas help to secure the impression material, allow free flow of the impression material, and serve as an internal endoskeleton framework. The device is hygienically, economically and conveniently disposable following a single use. The present device offers a further solution by providing a device that surrounds or partially surrounds a dental arch and is hollow in the occlusal area and without a separator sheet to section the configuration into upper and lower material containment chambers thereby allowing full surface to surface contact of the teeth and is hygienically, economically and conveniently disposable following a single use. Accordingly, the inventive dental impression device has a buccal support, a lingual support, and a joining section. The buccal support is disposed towards the buccal side of a dental arch; the lingual support is disposed towards the lingual side of a dental arch; and the joining section, which connects the buccal and lingual supports, is disposed posterior in the mouth's no bite region. The supports form impression material holding areas which hold and secure dental impression material. The supports form an open bite through area through which the lower and upper teeth's occlusal surfaces can make contact. Dental impression material supported in the holding area by the supports is disposed in the open bite area between the occlusal surfaces of the upper and lower teeth. The dental impression is then formed by a person making a closed bite into the impression material. The supports which surround or partially surround the dental arch, may be used to carry impression material to the mouth, hold the impression material in place during the impression process, become predominantly enveloped, surrounded, or buried within the impression material, and provide support and reinforcement, by way of forming an internal framework and endoskeleton. The device secures the set material for removal from the mouth and throughout the subsequent model preparation procedure. The device is inherently incapable of cross contamination due to the device being inexpensively fabricated and disposable following a single use. The device can hold dental impression pads through the heating process and carry the softened pads to the mouth for placement between the arches.

It is certainly possible to use the device with a separator sheet.

As part of a method to obtain a dental impression, the device is placed into the mouth surrounding a lower dental arch or a portion of a lower dental arch. A paste type dental impression material such as a silicone, a polyvinyl siloxane, a polyether, a polysulfide or any other such material, combination or composition that is basically a paste type consistency and is capable of being extruded and is set by chemical cure, is injected directly around the teeth and into the void area between the buccal and lingual arms of the device. The paste should be extruded, excessively thick onto the occlusal surfaces of the lower teeth. Alternatively, a device already containing thermoplastic material can be inserted into the patient's mouth. The dental impression material used with the device in this case can be a thermoplastic pre-form material such as a polycaprolactone, an ethylene vinyl acetate, a wax or any other such material, combination or composition that is basically hard at room temperature, is softened by heat and is set at body temperature in the mouth. This material can be pre-cut or pre-formed into pads or wafers that may be inserted between buccal and lingual arms of the device. It may also be softened and pressed between said arms. When the patient closes into a normal centric occlusion bite, the soft thermoplastic impression material extrudes out in all directions freely without constraint. It freely flows through, between and around the supports of the device, enveloping and burying the supports. The full extent of the flow is contained within the oral cavity and constrained buccally by the mucousal surface of the cheeks and lingually by the tongue. There is no separator sheet between the upper and lower teeth so that full surface-to-surface contact is achieved. There are no sidewalls to flex and relax so that when the material sets, it is in its final and fixed shape. After use and model preparation, the device is discarded. The disposable nature of the device eliminates the need to clean, strip and sterilize. It also totally eliminates the chance of cross contamination from one patient to the next.

PREFERRED EMBODIMENT

Referring now to the drawings, we see embodiments of the device. Each embodiment of the device has a buccal arm 1a, a lingual arm 1b and a buccal-lingual arm joining section 1c. The buccal arm 1a, lingual arm 1b and joining section 1c form a hollow area 2. The hollow area 2 is occupied by the teeth 3 when the device is fitted to a dental arch 4. See for example, FIG. 2a and FIG. 3a. The device may also have a handle 1e. The device forms impression material holding areas 1f and 1g. Applicant uses the term buccal to refer to that section of the support that is to be placed between the dental arch and the teeth and the cheeks or lips. Likewise, applicant uses lingual to refer to that section of the support that is to be placed between the dental arch and the tongue. Further, although applicant shows buccal supports 1a of the device as buccal arms 1a; lingual supports 1b as lingual arms 1b and the portion joining the arms 1c as a buccal-lingual arm joining section 1c, these parts could be other structures such as rails or guides.

Figure 1:
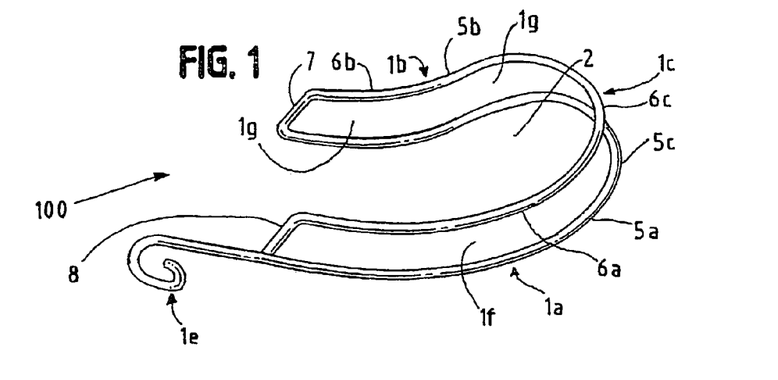
FIG. 1. is a bottom perspective view of one embodiment of a dental impression device of the present invention that is intended to partially surround a dental arch; the device is vertically repeating to form impression material holding areas.

The dental impression device or bite clip 100 as shown in FIG. 1 is vertically repeating. The device's buccal support 1a has a first and a second buccal portion (support) 5a, 6a; a first and a second lingual portion (support) 5b, 6b; and a first and second joining portion 5c, 6c. The portions 5a, 6a are vertically spaced from each other as are portions 5b, 6b. The joining portions 5c, 6c are also vertically spaced from each other. The first buccal 5a, first lingual 5b and first joining portion 5c are continuous with each other and form a first surrounding section. The second buccal 6a, second lingual 6b, and second joining portion 6c form a second surrounding section. The first and second surrounding sections are similarly shaped. The portions (supports) 5a, 6b bound the first impression material holding area 1f and supports 5b, 6b bound the second impression holding area 1g.

The first and second surrounding sections are joined by a bend 7 in the lingual support 1b of device 100. A bend 8 in the buccal support 1a of the device 100 provides a resilient physical contact between the first and the second surrounding sections.

Figure 2:
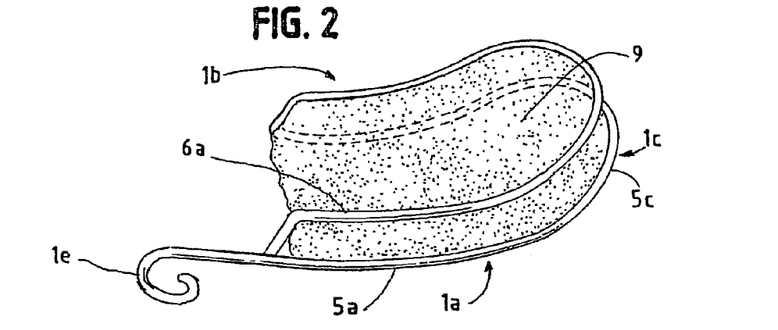
FIG. 2. is a bottom perspective view of the device shown in FIG. 1; the illustration shows the device containing a thermoplastic dental impression material.
Figure 2A:
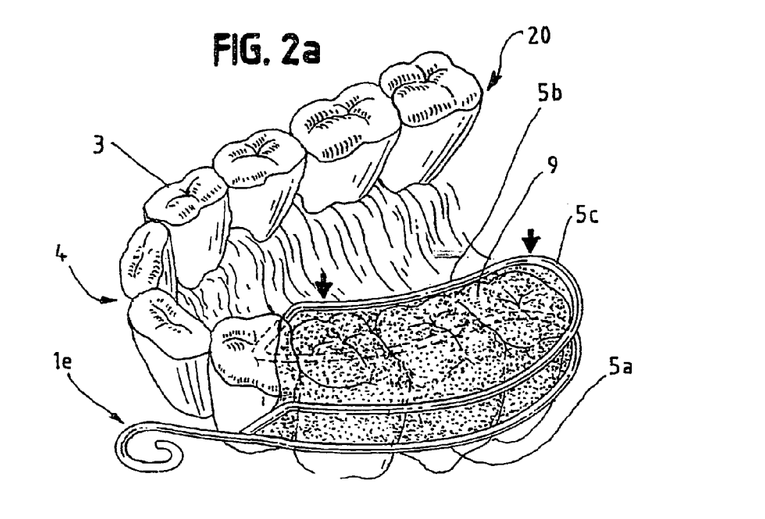
FIG. 2a. is a top perspective view of the device of FIG. 1 having the dental impression material of FIG. 2 inserted in the device, wherein the device and material covers a portion of a lower dental arch.

Dental impression device 100 is formed from a single continuous strand of wire. The impression device is formed so that its first and second buccal portions (supports) 5a, 6a extend along the buccal side of the dental arch 4, its first and second lingual portions (supports) 5b, 6b along the lingual side of the dental arch 4, and its first and second joining portions 5c, 6c preferably loop distally around the most posterior tooth so that they lie in a no bite interference area 20. Referring now to FIG. 2, a thermoplastic impression material 9, such as a polycaprolactone, an ethylene vinyl acetate, a wax or any other such material, combination or composition that is basically hard at room temperature, is softened by heat and is set at body temperature in the mouth, is pre-cut or pre-formed into pads, wafers, pre-forms or softened into a mass. The impression material 7 is inserted between the first and second surrounding sections of the device and is disposed between buccal support 1a and lingual support 1b so that the material at least partially fills the hollow 2. The material 9 is held in place by friction fit. A water or liquid bath is prepared for the device containing the material. The liquid is maintained at a temperature of approximately 150 degrees F. The device of the invention with the thermoplastic material 9 in place, FIG. 2, is submerged into a hot water bath for approximately one (1) minute. Alternatively, the device of the invention with the thermoplastic material 9 in place, FIG. 2, may be heated using any conventional means such as over a Bunsen burner flame, or with a small portable torch, or inside an autoclave, microwave or conventional oven, or by use of a specially designed and manufactured heating appliance. The important considerations during the heating phase are related to the specific type and trade brand of thermoplastic material used. In all cases the manufacturer's recommended time and temperature procedures for softening should be followed. When the thermoplastic material is at the correctly softened consistency, the device 100 with the material 9 in place is carried to and inserted into the mouth of the dental patient. The device is positioned with the central area 2 (bite through area) and the material 9 over the lower arch, between the occlusal surface of the upper (maxillary) and lower (mandibular) teeth. Care is taken to insure that the device is positioned such that the joining section 1c is beyond the hamular notch. When the device is correctly positioned in the mouth the patient is instructed to close fully into a full surface to surface centric occlusion bite.

Figure 3:
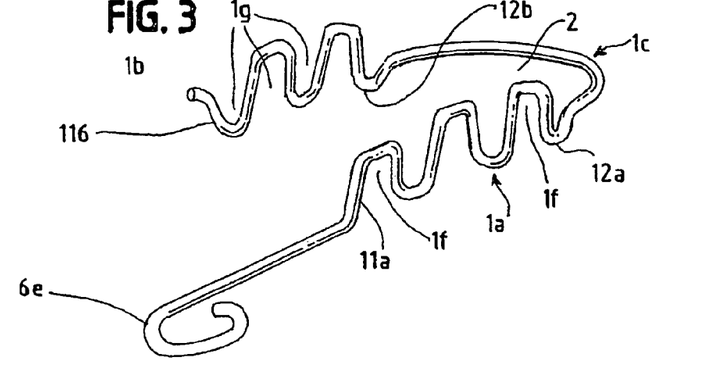
FIG. 3. is a bottom perspective view of an alternative embodiment of the dental impression device of the present invention with its buccal and lingual supports (arms) vertically extended to form the impression material holding area.
Figure 3A:
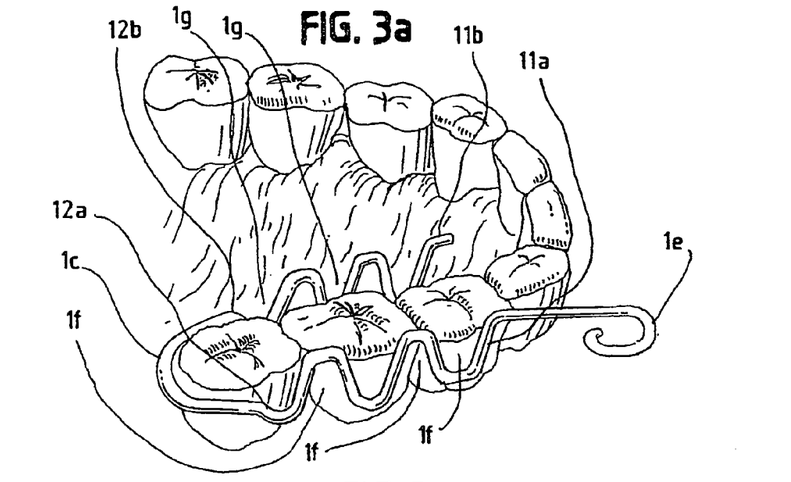
FIG. 3a. is a top side perspective view of the device of FIG. 3 wherein the device is surrounding a portion of a lower dental arch, and wherein no impression material has been applied.

When the patient bites into the thermoplastic material, the material instead of being pressurized and forced against some constraining buccal and lingual sidewalls causing them to flex outwardly or randomly in distorted directions, is simply free to flow through, over, under and around the continuous buccal support 1a, and lingual support 1b. The supports and joining section remain in a relatively static position. The nature and flow characteristics of thermoplastic impression materials are such that the flow is not so fluid that the material will flow as an uncontrolled liquid. The soft plastic consistency of the material allows for a bolus form to be constrained and shaped by the mucous surface of the cheeks and the pressure of the underlying buccal muscle. When the material is set and the device is being removed from the mouth, the material that has flowed over, under, through and around the portions of the device is now nearly impossible to separate from the device because these portions of the device are buried within, supporting and reinforcing the correct, dimensionally accurate, unaltered impression material from an internal position and acting as an endoskeletal framework. Having at least portions of the supports imbedded in the material prevents the material from separating from the device during the critical model preparation phase. Additionally, the free flow of material over, under, through and around the device means an absence of sidewall flexing and an absence of containment sidewalls being distorted under bite pressure which return, by memory, to their original shape, bringing various areas of the impression into permanent distortion. Referring now to FIG. 3, we see an alternative embodiment. FIG. 3 shows its buccal support 1a with at least a first portion 11a vertically extended. Buccal support 1a also has at least a second portion 12a vertically extended. The buccal extended portions 11a, 12a are laterally spaced from each other. Likewise, lingual support 1b has a first portion 11b and a second portion 12b both vertically extended. Again these extended portions 11b, 12b are laterally spaced from each other. The vertically extended portions 11a, 12a and 11b, 12b bound the holding areas 1f and 1g. To the contrary, in FIG. 2 vertically repeating portions 5a, 6a and 5b, 6b bounded the holding areas 1f and 1g.

Figure 4:
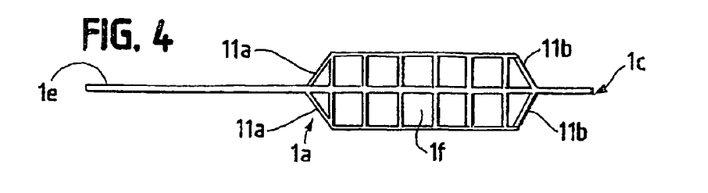
FIG. 4. is a right buccal side view of an alternative embodiment of the device of the present invention with the device's supports (arms) having a lattice configuration to form the impression material holding areas.
Figure 5:
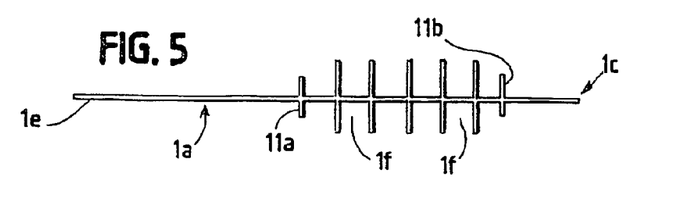
FIG. 5. is a right buccal side view of an alternative embodiment of the device of the present invention with the device's supports (arms) having a wiry picket configuration to form the impression material holding areas.
Figure 6:
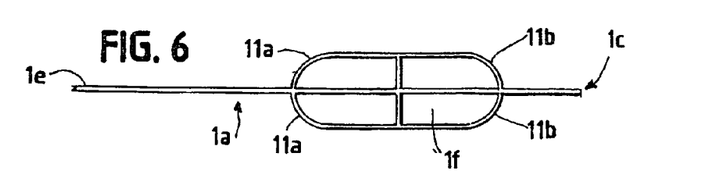
FIG. 6. is a right buccal side view of an alternative embodiment of the device of the present invention with the device's supports having a wiry window configuration to form the impression material holding areas.
Figure 7:
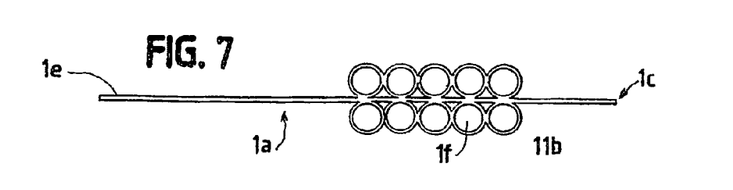
FIG. 7. is a right buccal side view of an alternative embodiment of the device of the present invention with the device's supports having a wiry loop configuration to form the impression material holding areas.
Figure 8:
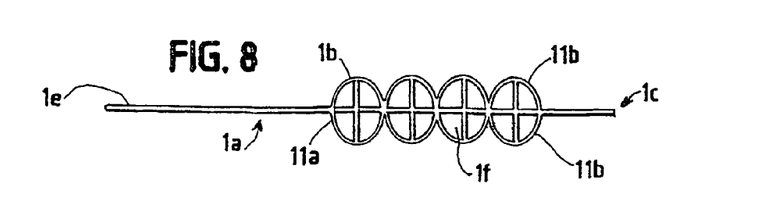
FIG. 8. is a right buccal side view of an alternative embodiment of the device of the present invention with the device's supports having a combination curve, loop, angle, pattern, window configuration to form the impression material holding areas.
Figure 9:
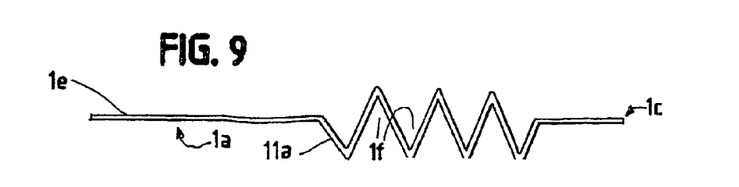
FIG. 9. is a right buccal side view of an alternative embodiment of the device of the present invention with the device's supports vertically extended.

Many other configurations of vertically extended buccal 1a and lingual arms 1b are possible. In FIG. 4, we see a lattice buccal arm, FIG. 5 a picket buccal arm, FIG. 6 a buccal arm with bends, FIG. 6, a buccal arm with windows, FIG. 7, a buccal arm with loops, FIG. 8, a buccal arm with arcs, FIG. 8 a buccal arm with curves, FIG. 8 a buccal arm with spokes, FIG. 9, a weave buccal arm, FIG. 8, a pattern buccal arm. Each of the examples FIGS. 4 thru 9 shows a right sided buccal view. The buccal view shows the buccal arm 1a, handle 1e and joining section 1c. The opposite lingual arms 1b, not shown, in the above constructions have the same shape as the shown buccal arms 1a.

Figure 10:
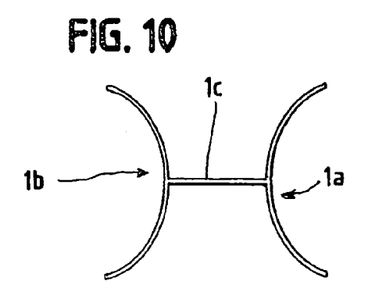
FIG. 10. is a front view of an alternative embodiment of the device of the present invention showing the supports (buccal and lingual arms) having outwardly curved portions.
Figure 11:
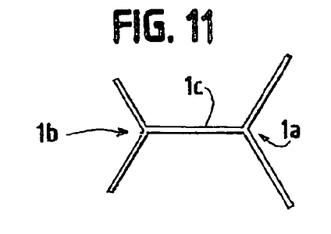
FIG. 11. is a front view of an alternative embodiment of the device of the present invention with the buccal and lingual arms having outwardly angled portions.
Figure 12:
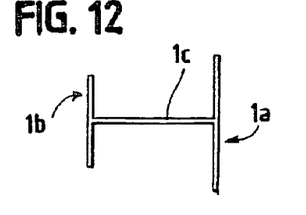
FIG. 12. is a front view of an alternative embodiment of the device of the present invention with the buccal and lingual arms vertically extended to be perpendicular.
Figure 13:
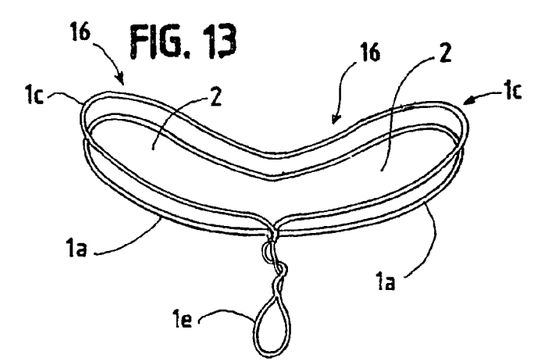
FIG. 13. is a perspective view of an alternative embodiment of the present invention that surrounds an entire dental arch buccally and lingually and the device's supports are vertically repeating and form the impression material holding areas.

A buccal 1a and lingual arm 1b that is vertically extended may be outwardly curved as illustrated in FIG. 10 or outwardly angled as in FIG. 11 or it may be perpendicular as shown in FIG. 12. Each of the illustrations FIGS. 10 thru 12 show cross-sectional front views. The views show the joining section 1c, the buccal arm 1a and the lingual arm 1b.

Figure 3B:
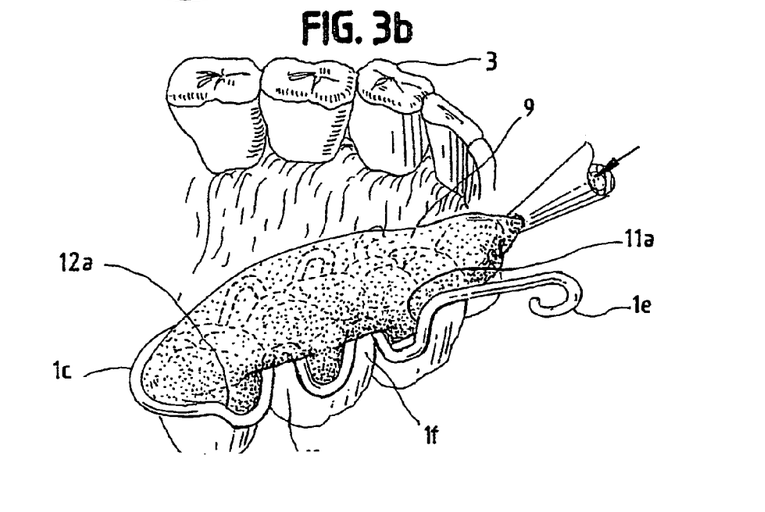
FIG. 3b. is a similar perspective and the same device as shown in FIG. 3a with the dental impression material being added.
Figure 3C:
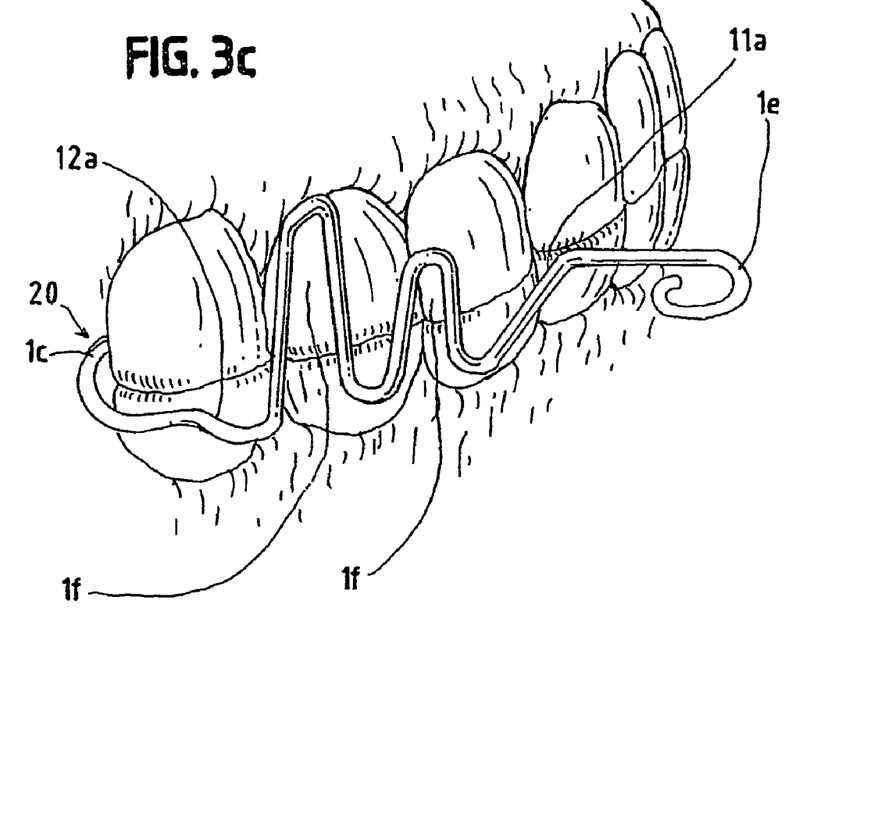
FIG. 3c. is a top side perspective view of the device in FIG. 3a wherein the upper and lower dental arch are in a closed bite position and a portion thereof is surrounded by the dental device, no impression material has been applied.
Figure 3D:
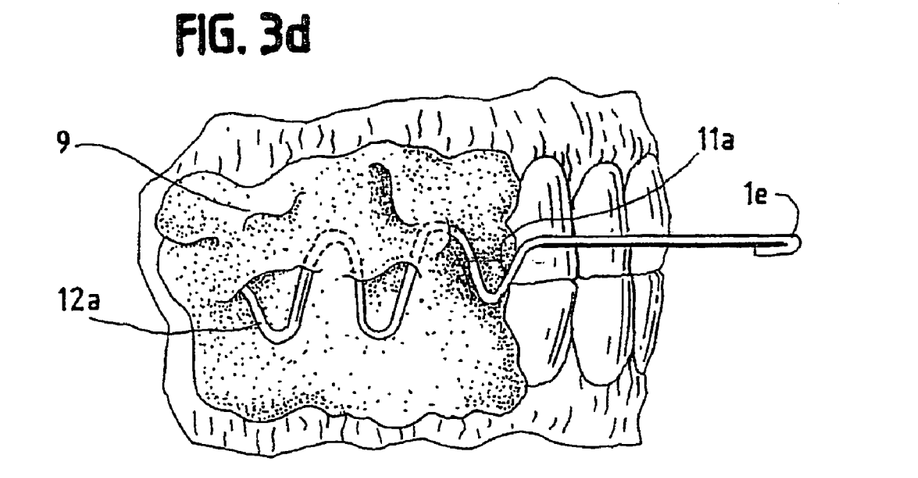
FIG. 3d. is a similar side perspective view as shown in 3c, with the same device shown in FIG. 3c, with the dental impression material already having been applied.

In another method of practicing the invention, the device, as illustrated in FIG. 1, as illustrated in FIGS. 3 thru 9, or a device with the same performance characteristics as disclosed above, can be placed into the mouth of the dental patient and is seated around (for full arch impression) or partially around (for quadrant impression) the lower arch. The device may rest lingually on the floor of the mouth and buccally in the vestibules. Care is taken to insure that the device is positioned such that the joining section 1c is beyond the hamular notch. By use of a traditional syringe or common dual cartridge motionless mixer gun, a paste type, chemical cure impression material such as a silicone, a polyvinyl siloxane, a polyether, a polysulfide or any other such material, combination or composition that is basically a paste type consistency and is capable of being extruded and is set by chemical cure or light energy cure can be injected directly onto the occlusal surface of the lower teeth. See FIG. 3b. The material is excessively extruded into a pile. Extra material is also injected into the free space between the teeth and the arms of the device. Because the impression material is to an extent, stackable with a consistency similar to toothpaste, it will remain fairly well in place. With the material in place the patient is instructed to close into a normal full contact centric occlusion bite. When the patient's mouth is fully closed the dentist may use the handle portion 1e to adjust the device slightly upward into the soft paste so that it rests midway between the upper and lower teeth while they are in full contact. If the device was formed without a handle, the dentist may use a hemostat or similar device to grip a portion of the device for movement or adjustment. No adjustment may be necessary. When the patient bites into the paste type material, the material instead of being pressurized and forced against some constraining buccal and lingual sidewalls, is free to flow through, over, under and around the supports. The supports (arms) remain in a relatively static position.

The nature and flow characteristics of paste type, chemical cure impression materials are such that the flow is not so fluid that the material will flow as an uncontrolled liquid. The soft plastic, tenacious paste consistency of the material allows for a bolus form to be constrained and shaped by the mucous surface of the cheeks and the pressure of the underlying buccal muscle, and by the position and placement of the tongue at rest when the mouth is closed. When the material is set and the device is being removed from the mouth, the device now nearly impossible to separate from the impression material because at least portions of the device are buried within, supporting and reinforcing the correct, dimensionally accurate, impression material from an internal position and acting as an endoskeletal framework. This internal support and reinforcement also prevents the material from separating from the device during the critical model preparation phase. The disclosed use of the device and the method of the invention gives the resultant chemically cured impression the same benefits of improved accuracy as the use of the device with thermoplastic impression materials as disclosed in FIG. 2 and is disposable following a single use.

When a dentist desires to obtain a dental impression of a patient's dental arch a pre-formed or pre-manufactured device of the present invention may be used or the dentist may manually bend and form a length of wire or plastic into the device of the invention. In either case the device is constructed to surround or partially surround the dental arch with free spacing approximately ⅛ to ⅜ inches all around the teeth. Preferably the material is a steel or stainless steel wire that may be in a range of between 10 gauge (0.101")

and 28 gauge (0.0126"). Alternatively an aluminum or copper wire in the same gauge range is acceptable. Additionally the wire may be coated or insulated with a plastic covering similar to insulated electrical wire. The wire may be hard or ductile. If the wire is hard, it should be preferably stiff enough to hold its shape while impression material passes around and through its form. If the wire is soft and ductile it should be preferably soft and ductile to the point of having no return memory. Effectively, if the soft wire is distorted as impression material passes over, around and through its form, it should be a permanent distortion and remain in the distorted position throughout the setting of the material, i.e., the device is not trying to spring back to its original shape. Wire that is soft and ductile has an advantage over a wire that is hard and stiff, specifically, the wire may be easily adjusted, reshaped and sized to the individual patient. In clinical trials, excellent results were obtained using a variety of both hard and soft wires. There are some thin, wiry, sinuous plastics suitable to work in a construction of the device and in those instances they could be acceptable and possibly preferred. The most preferred material is 10 (0.101"), 12 (0.0808") 14 (0.0640"), 16 (0.0508") and 18 (0.0403") gauge, hardened stainless steel wire that is vinyl or nylon coated. Although the preferred material of the device is disclosed in terms of gauge due to it being commonly understood within the profession, the wiry, sinuous device need not be fabricated from round stock. Round stock that has been flattened or flat stock in the same general gauge dimension, metal and/or plastic or plastic coated or material that is ribbon or spiral shaped or braided is certainly useable and may be preferable to some dentists on specific occasions. Effectively, any material shape or appearance that is formed, stamped, bent, molded, pressed, assembled, electro-welded or created into a wiry, sinuous, picket or lattice configuration of metal and/or plastic that surrounds or partially surrounds a dental arch for the purpose of a dental impression and achieves the basic objective of being predisposed to allow the free flow of impression material over, under, through and in between such that at least the portions of the supports will be predominantly enveloped by the impression material to form an internal, endoskeleton framework, and is hygienically, economically and conveniently disposable following a single use could be acceptable.

It should be recognized that while the invention has been described in relation to a preferred embodiment thereof, those skilled in the art may develop a wide variation of structural details without departing from the principles of the invention. Accordingly, the appended claims are to be construed to cover all equivalents falling within the scope and spirit of the invention.

What is claimed is:

1. A dental impression device comprising:
    a buccal support having an outward facing surface adapted to be positioned toward a buccal side of at least a portion of a dental arch;
    a lingual support having an inward facing surface adapted to be positioned toward a lingual side of at least a portion of a dental arch;
    a portion joining the buccal support and the lingual support;
    a bite through area through which at least a portion of the dental arch may pass bounded by said buccal support, said lingual support and said portion joining;
    said buccal support includes a first portion and a second portion separated by an open through space passing through said buccal support, said open through space comprises an area greater than the area of the buccal outward facing surface to form a first impression material area; and
    said lingual support includes a first portion and second portion separated by an open through space passing through said lingual support, said open through space comprises an area greater than the area of the lingual inward facing surface, to form a second impression material area;
    and wherein said device is disposable.

2. The dental impression device of claim 1 wherein said supports are made from material selected from the group consisting of: metal, plastic, and combinations thereof.

3. The dental impression device of claim 1 wherein the buccal support first portion is a first buccal arm and the buccal support second portion is a second buccal arm, said first and second buccal arms are spaced vertically to form said first impression material area; and said lingual support first portion is a first lingual arm, said lingual support second portion is a second lingual arm, said first and second lingual arms are spaced vertically to form said second impression material holding area.

4. The dental impression device of claim 1, further comprising:
    dental impression material in both said impression material areas.

5. The dental impression device of claim 4 wherein said dental impression material is selected from a group of materials consisting of: polycaprolactone, ethylene vinyl acetate, wax, and tripolyvinylene.

6. The dental impression device of claim 4 wherein the dental impression material has a structural configuration selected from a group of structures consisting of: pads, wafers, and pre-forms.

7. The dental impression device of claim 4 wherein when said dental impression device is sized to be inserted in a position wherein said device is oriented such that said buccal support is positioned toward a buccal side of a dental arch, the lingual support is positioned toward a lingual side of the dental arch, the dental impression material is covering at least a portion of an occlusal area of the dental arch.

8. The dental impression device of claim 4 wherein said dental impression material is selected from the group consisting of a paste-type material, silicone, polyvinyl siloxane, polyether and polysulfide.

9. The dental impression device of claim 1 wherein the buccal support first portion is vertically extended, and said buccal support second portion is vertically extended, said first and second buccal portions are laterally spaced from each other to at least partially bound said first impression area, and/or
    said lingual support first portion and said lingual support second portion are both vertically extended, said first and second lingual portions are laterally spaced to at least partially bound said second impression area.

10. The dental impression device of claim 1
    wherein said dental impression device is malleable so that its shape is adjustable by hand.

11. A method of taking a dental impression comprising the steps of:
    providing buccal support and lingual support which defines an open bite through area there between;
    positioning said buccal support toward a buccal side of at least a portion of a dental arch;

positioning said lingual support toward a lingual side of at least a portion of a dental arch;

positioning at least a portion of said dental arch within said open area;

after positioning said dental arch within said open area, applying impression material over a surface wherein the surface forms parts of a person's bite surface; and wherein at least some of the impression material is between the buccal and lingual supports;

obtaining a dental impression;

removing said supports from said dental arch.

* * * * *